(12) United States Patent
Potappel-Van 'T Land et al.

(10) Patent No.: US 10,124,016 B2
(45) Date of Patent: Nov. 13, 2018

(54) IMMUNE SYSTEM STIMULATING NUTRITION

(71) Applicant: N.V. Nutricia, Zoetermeer (NL)

(72) Inventors: Belinda Potappel-Van 'T Land, Kootwijk (NL); Leon Matthieu Johannes Knippels, Utrecht (NL); Alma Jildou Nauta, Utrecht (NL); Johan Garssen, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 15/406,361

(22) Filed: Jan. 13, 2017

(65) Prior Publication Data

US 2017/0296563 A1    Oct. 19, 2017

Related U.S. Application Data

(63) Continuation of application No. 12/997,527, filed as application No. PCT/NL2009/050333 on Jun. 12, 2009, now abandoned.

(30) Foreign Application Priority Data

Jun. 13, 2008  (NL) ................. PCT/NL2008/050375
Oct. 31, 2008  (EP) .................................... 08168054

(51) Int. Cl.
| | | |
|---|---|---|
| *A01N 63/00* | (2006.01) | |
| *A61K 31/702* | (2006.01) | |
| *A61K 35/745* | (2015.01) | |
| *A23L 33/00* | (2016.01) | |
| *A23L 33/135* | (2016.01) | |
| *A61K 31/733* | (2006.01) | |
| *A61K 35/744* | (2015.01) | |
| *A61K 38/01* | (2006.01) | |

(52) U.S. Cl.
CPC .......... *A61K 31/702* (2013.01); *A23L 33/135* (2016.08); *A23L 33/40* (2016.08); *A61K 31/733* (2013.01); *A61K 35/744* (2013.01); *A61K 35/745* (2013.01); *A61K 38/017* (2013.01); *A61K 38/018* (2013.01); *A23V 2002/00* (2013.01)

(58) Field of Classification Search
CPC .............. A61K 2300/00; A61K 31/702; A23V 2002/00; A23V 2200/324; A23V 2200/3202
See application file for complete search history.

(56) References Cited

U.S. PATENT DOCUMENTS

| | | |
|---|---|---|
| 4,110,476 A | 8/1978 | Rhodes |
| 6,358,521 B1 | 3/2002 | Izvekova et al. |
| 7,410,653 B1 | 8/2008 | Blareau et al. |
| 8,119,379 B2 | 2/2012 | Blareau et al. |
| 8,715,769 B2 | 5/2014 | Schmitt et al. |
| 2004/0072794 A1 | 4/2004 | Kaup et al. |
| 2005/0180962 A1 | 8/2005 | Raz et al. |
| 2006/0018890 A1 | 1/2006 | Isolauri et al. |
| 2006/0233773 A1 | 10/2006 | Herz et al. |
| 2007/0104700 A1* | 5/2007 | Garcia-Rodenas ......... A61K 31/202 424/93.45 |
| 2007/0160589 A1 | 7/2007 | Mattson |
| 2008/0268099 A1 | 10/2008 | Blareau et al. |
| 2010/0278781 A1 | 11/2010 | Hougee et al. |
| 2011/0097437 A1 | 4/2011 | Knol et al. |
| 2013/0189398 A1 | 7/2013 | Rosado Loria et al. |

FOREIGN PATENT DOCUMENTS

| | | |
|---|---|---|
| EP | 1 020 123 A1 | 7/2000 |
| EP | 1 145 643 A1 | 10/2001 |
| EP | 1 320 375 B1 | 6/2003 |
| EP | 1 364 586 A1 | 11/2003 |
| EP | 1 535 520 A1 | 6/2005 |
| EP | 1 597 978 A1 | 11/2005 |
| EP | 1 685 763 A1 | 8/2006 |
| EP | 1 776 877 A1 | 4/2007 |
| EP | 1 815 755 B1 | 8/2007 |
| EP | 2 520 181 A1 | 11/2012 |
| WO | WO-01/01785 A1 | 1/2001 |
| WO | WO-01/64225 A1 | 9/2001 |
| WO | WO-02/26242 A2 | 4/2002 |
| WO | WO-2004/052121 A1 | 6/2004 |
| WO | WO2004052121 * | 6/2004 |
| WO | WO-2004/069156 A2 | 8/2004 |
| WO | WO2004069156 * | 8/2004 |
| WO | WO-2004/093898 A2 | 11/2004 |
| WO | WO-2004/093899 A1 | 11/2004 |
| WO | WO2004093899 * | 11/2004 |
| WO | WO-2004/112509 A2 | 12/2004 |
| WO | WO-2005/039319 A1 | 5/2005 |
| WO | WO-2005/039319 A2 | 5/2005 |
| WO | WO-2005/039597 A2 | 5/2005 |
| WO | WO-2006/069918 A1 | 7/2006 |
| WO | WO-2006/087391 A1 | 8/2006 |

(Continued)

OTHER PUBLICATIONS

Menard et al., "Bifidobacterium breve and *Streptococcus thermophilus* Secretion Products enhance T Helper 1 immune Response and Intestinal Barrier in Mice", 2005, Exp Biol Med, 230:749-756.*

(Continued)

*Primary Examiner* — Barry A Chestnut
(74) *Attorney, Agent, or Firm* — Gilberto M. Villacorta; Sunit Talapatra; Foley & Lardner LLP

(57) ABSTRACT

Disclosed is a nutritional composition comprising a combination of non-digestible oligosaccharides and a product obtained by incubating an aqueous substrate by bifidobacteria and optionally a product obtained by incubating an aqueous substrate by *S. thermophilus*. Said combination synergistically improves the immune system by stimulating the Th1 response, and/or decreasing the Th2 response, improving the vaccination response, improving the resistance against infections and/or decreasing allergy.

9 Claims, No Drawings

(56) References Cited

FOREIGN PATENT DOCUMENTS

| WO | WO-2006/091103 A2 | | 8/2006 |
|---|---|---|---|
| WO | WO2006091103 | * | 8/2006 |
| WO | WO-2007/045502 A1 | | 4/2007 |
| WO | WO-2007/046698 A1 | | 4/2007 |
| WO | WO-2007/067053 A1 | | 6/2007 |
| WO | WO-2008/153377 A1 | | 12/2008 |
| WO | WO-2008/153391 A2 | | 12/2008 |
| WO | WO2008153377 | * | 12/2008 |
| WO | WO-2009/151329 A1 | | 12/2009 |
| WO | WO-2009/151330 A1 | | 12/2009 |
| WO | WO-2010/008278 A1 | | 1/2010 |
| WO | WO-2010/070613 A2 | | 6/2010 |
| WO | WO-2012/078030 A1 | | 6/2012 |
| WO | WO-2012/078039 A1 | | 6/2012 |

OTHER PUBLICATIONS

U.S. Appl. No. 15/278,475, Unpublished, Unassigned.
U.S. Appl. No. 14/952,440, US 2016-0206658 A1, Elizabeth A. Gwartney.
U.S. Appl. No. 13/991,802, US 2013-0337105 A1, Bhaskar Mukhopadhyay.
U.S. Appl. No. 14/407,907, US 2015-0132365 A1, Agnieszka Boesen.
U.S. Appl. No. 15/033,543, Unpublished, Kelly Jo Bekker.
Alm, L., "Effects of Fermentation on Curd Size and Digestibility of Milk Proteins in Vitro of Swedish Fermented Milk Products," Journal of Diary Science, vol. 65, No. 4, pp. 509-514, Apr. 1982.
European Search Report in Application No. 08168054.8 dated May 8, 2009.
Fanaro et al., "Galacto-oligosaccharides and long-chain fructo-oligosaccharides as prebiotics in infant formulas: A review", Acta Paediatrica, 94 (Suppl 449), 2005, 22-26.
Heyman et al., "Effects of specific lactic acid bacteria on the intestinal permeability to macromolecules and the inflammatory condition," ACTA Paediatrica, vol. 94 (Suppl. 449), pp. 34-36 (2005).
International Search Report in PCT/NL2009/050333 dated Aug. 14, 2009.
Kirjavainen et al., "Probiotic Bacteria in the Management of Atopic Disease: Underscoring the Importance of Viability," Journal of Pediatric Gastoenterology and Nutrition, 36:223-227 (2003).
Life Start®—Dairy (1.25 oz. powder), Natren, The Probiotic Specialist Recognized Worldwide, 2 pgs., (2006).
McVay et al., "Formula Fortified With Live Probiotic Culture Reduces Pulmonary and Gastrointestinal Bacterial Colonization and Translocation in a Newborn Animal Model," Journal of Pediatric Surgery, 43:25-29 (2008).
Menard et al. "Bifidobacterium breve and *Streptococcus thermophiles* secretion products enhance T helper 1 immune response and intestinal barrier in mice", 2005, Exp. Biol. Med. vol. 230, pp. 749-756.
Petay et al., ( WO 2004093899)—Google Machine Translation WIPO, Sep. 28, 2012.
Prosky L, et al., "Determination of Insoluble, Soluble, and Total Dietary Fiber in Foods and Food Products: Interlaboratory Study," J. Assoc. Off. Anal. Chem., 1988, vol. 71, No. 5, pp. 1017-1023.
Reeves P, et al., "Development and Testing of the AIN-93 Purified Diets for Rodents: Results on Growth, Kidney Calcification and Bone Mineralization in Rats and Mice," Journal of Nutrition, 1993, pp. 1923-1993, vol. 123, No. 11.
Sambrook, J., et al.. "Molecular Cloning, A Laboratory Manual," 2nd ed., Cold Spring Harbor (N.Y.) Laboratory Press, 1989.
Savino et al., "Reduction of crying episodes owing to infantile colic: a randomized controlled study on the efficacy of a new infant formula", European Journal of Clinical Nutrition, 2006, vol. 60, pp. 1304-1310.
Scardovi V., "Genus *Bifidobacterium* Orla-Jensen 1924, 472AL," In: Bergey's Manual of Systematic Bacteriology, vol. 2, Williams & Wilkins, Baltimore, 1984, pp. 1418-1434.
Thibault H et al. "Effects of Long-Term Consumption of a Fermented Infant Formula (With Bifidobacterium Breve C50 and *Streptococcus thermophilus* 065) on Acute Diarrhea in Healthy Infants", Journal of Pediatric Gastroenterology and Nutrition, Raven Press, New York, NY vol. 39, No. 2, Aug. 1, 2004.
Vass, A. et al., "Experimental Study of the Nutritional Biological Characters of Fermented Milks," Acta Medica Hungarica, vol. 41, Nos. 2-3, pp. 157-161, 1984.
Vergnolle, "Clinical relevance of proteinase activated receptors (PARS) in the gut", Gut, 2005, vol. 54, pp. 867-874.

* cited by examiner

IMMUNE SYSTEM STIMULATING NUTRITION

CROSS-REFERENCE TO RELATED APPLICATIONS

This application is a Continuation application of U.S. patent application Ser. No. 12/997,527, filed Apr. 8, 2011, which is the U.S. National Phase of International Patent Application No. PCT/NL2009/050333, filed Jun. 12, 2009, published on Dec. 17, 2009 as WO 2009/151331 A1, which claims priority to European Patent Application No. 08168054.8, filed Oct. 31, 2008 and International Patent Application No. PCT/NL2008/050375, filed Jun. 13, 2008. The contents of these applications are herein incorporated by reference in their entirety.

FIELD OF THE INVENTION

The present invention relates to a nutrition for improving the immune system response and a process for its preparation.

BACKGROUND OF THE INVENTION

The immune system has different possible ways of reacting. A decisive step for the type of immune response is the stimulation of different T-cell subpopulations. So called Th1 cells predominantly produce cytokines that stimulate a cellular immune response (IFN-y, IL-12, IL-2), for instance to pathogens and vaccines. In contrast, Th2 cells predominantly produce IL-4, IL-5 and IL-10. These cytokines boost an IgE-mediated allergic reaction and inflammation. Th1- and Th2-related cytokines act antagonistically and the Th1 and Th2 responses are under normal physiological circumstances in a well-controlled balance. Neither the Th1 nor the Th2 response prevails. If the responses are in imbalance, the dominance of either Th1 or Th2 immune responses play a role in several pathological conditions.

WO 2005/039319 and WO 2006/091103 relate to a preparation comprising *Bifidobacterium breve* and a mixture of non-digestible carbohydrates for non- or partially breast-fed infants as well as the use thereof for the treatment or prevention of immune disorders in non- or partially breast-fed infants. WO 2005/039597 relates to the use of acid oligosaccharide and neutral oligosaccharide for enhancing the immune system and the treatment and/or prevention of immune system related disorders. WO 01/642255 relates to a nutritional composition comprising a prebiotic for enhancement of an immune response. WO 2004/0938998 and WO 2004/0938999 relate to an immunomodulatory products obtained from a *Bifidobacterium* culture.

Much effort is dedicated to find further solutions for balancing and stimulating the immune system.

SUMMARY OF THE INVENTION

The present inventors have surprisingly found that a combination of i) a product obtained by incubating an aqueous substrate with bifidobacteria, wherein the substrate is at least one selected from the group consisting of milk, milk protein, whey, whey protein, whey protein hydrolysate, casein hydrolysate, and lactose and subsequently inactivating the bifidobacteria by heating the incubated mixture and/or removing the bifidobacteria cells from the incubated mixture by centrifugation and/or filtration and ii) at least two different non-digestible carbohydrates, wherein at least one, preferably two, is selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, raffinose, lactosucrose, sialic acid comprising oligosaccharides and uronic acid oligosaccharides synergistically stimulates the immune-system. It was found that the present preparation, i.e. the preparation comprising the combination as described above, lowered the Th2 response and/or increased the Th1 response. The effect observed was unexpectedly higher than the sum of the effects of the single components.

In two different experimental animal models, the unexpectedly higher effect was found. An increased response in delayed type hypersensitivity reaction, indicative for an increased Th1 response, was observed after vaccination with an influenza vaccine in animals having consumed the present preparation, compared to animals having consumed the single components. A combination of a product obtained by incubating a substrate with bifidobacteria and a product obtained by incubating with streptococci plus two non-digestible carbohydrates resulted in an even higher response in delayed type hypersensitivity reaction.

A decreased response in immediate type hypersensitivity reaction, indicative for a decreased Th2 response, was observed after exposure to an allergen via the lungs, in animals having consumed the present preparation, compared to animals having consumed the single components.

The synergistic effect between the combination of the ingredients i) and ii) as defined above is surprising. It cannot be explained by a symbiotic effect, wherein the non-digestible carbohydrates (ii)) are specifically stimulating the growth of the beneficial micro-organisms present in the same preparation, since no living cells of bifidobacteria are present in the present preparation. Removal and/or inactivation of living bifidobacteria cells has the advantage that the preparation can be pasteurised and/or sterilised, consequently reducing the chance of contamination with harmful micro-organisms. This is especially advantageous in infants, since infants have an increased intestinal permeability. Additionally, since the bifidobacteria are removed or inactivated they cannot cause infections themselves.

A further advantage is that the dose of bioactive components received by each human subject can be better controlled. Also advantageously storage of the product is more easily and with reduced costs. Furthermore, advantageously no post-acidification occurs in stored products, thereby avoiding adverse effects relating to coagulation of proteins and adverse taste. Still a further advantage is that inactivated and/or removed bifidobacteria no longer able to breakdown and consume the non-digestible carbohydrates.

The present preparation is especially advantageous for human subjects shaving a reduced Th1 response in comparison with healthy adults, in particular newborn infants, elderly humans suffering from immunosenescence, humans suffering from AIDS or being infected with the Human Immunodeficiency Virus, and cancer patients that are or have been subjected to chemotherapy, radiation and cancer patients that are cachectic.

The present preparation is especially suitable for the treatment and/or prevention of diseases which can be prevented and/or treated by a decrease in Th2 response, in particular allergy, atopic dermatitis, asthma, food allergy, allergic rhinitis (e. g. pollen allergy), dust mite allergy and other forms of hypersensitivity like systemic anaphylaxis and acute urticaria.

The present preparation is suitable for treatment and/or prevention of infections, and/or for supporting vaccination response before, during and/or after vaccination.

DETAILED DESCRIPTION OF THE INVENTION

The present invention concerns a process for the manufacture of a preparation comprising the steps of:

a: incubating an aqueous substrate with bifidobacteria, wherein the substrate comprises at least one selected from the group consisting of milk, milk protein, whey, whey protein, whey protein hydrolysate, casein hydrolysate, and lactose to obtain an incubated mixture;

b: inactivating the bifidobacteria by heating the incubated mixture and/or removing bifidobacteria cells from the incubated mixture by centrifugation and/or filtration; and c: combining a composition comprising the mixture obtained in step a or obtained in step b, preferably obtained in step b with at least two different non-digestible carbohydrates, wherein at least one, preferably two, is selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, raffinose, lactosucrose, sialic acid comprising oligosaccharides and uronic acid oligosaccharides.

In one aspect, the present invention concerns a preparation obtainable by the process according to the present invention. In one embodiment the invention concerns a nutritional composition comprising or consisting of the preparation obtainable by the process according to the present invention.

Also the invention concerns a method for the treatment and/or prevention of a disease in a mammal, said method comprising administering the present preparation to the mammal.

Also the invention concerns a method for providing nutrition to an infant, said method comprising administering the present preparation or nutritional composition comprising the present preparation to the infant.

Process Comprising Incubating a Substrate With Bifidobacteria

The present invention concerns a preparation obtainable or obtained by incubating an aqueous substrate with bifidobacteria, wherein the aqueous substrate comprises at least one selected from the group consisting of milk, milk protein, whey, whey protein, whey protein hydrolysate, casein hydrolysate, and lactose (hereinafter referred to as step (a)). The incubated mixture obtained or obtainable in step (a) is subjected to a step (b) comprising an inactivation step by heat treatment and/or removal step of the bifidobacteria cells by centrifugation and/or filtration. Step (b) is performed in order to reduce the amount of living bifidobacteria in the preparation, preferably by at least 90%, more preferably by at least 99%.

In one embodiment the incubation step comprises a fermentation step and/or bioconversion step. During fermentation the aqueous substrate is fermented by the bifidobacteria. During bioconversion the aqueous substrate is bioconversed by the bifidobacteria.

The preparation obtained or obtainable by (hereafter wherever only 'obtained' is mentioned, also 'obtainable by' is meant) the present process preferably comprises bacterial cell fragments like glycoproteins, glycolipids, peptidoglycan, lipoteichoic acid (LTA), lipoproteins, DNA, and/or capsular polysaccharides. These fragments evoke an immunological response. It is of advantage to use the product obtained by incubating an aqueous substrate comprising at least one selected from the group consisting of milk, milk protein, whey, whey protein, whey protein hydrolysate, casein hydrolysate and lactose with bifidobacteria and subsequently inactivating and/or removing the bifidobacteria, since this will result in a higher concentration of bacterial cell fragments. Upon incubation of the aqueous substrate with the bifidobacteria, additional bio-active compounds may be formed, such as organic acids, bioactive peptides and/or oligosaccharides, which stimulate the immune system. When commercial preparations of probiotics are used, the probiotic bacterial cells are usually washed and separated from the aqueous growth medium that comprised the bacterial cell fragments, thereby strongly reducing or even eliminating the supernatant of the incubates substrate comprising the bacterial cell fragments. In the present invention this is not the case. The presence of intact cells (living or dead) is not necessary for the immune response; the aqueous substrate itself, after the present incubation step with bifidobacteria, has already beneficial effects on the immune system.

Bifidobacteria

Bifidobacteria used for the present process are preferably provided as a mono- or mixed culture. Bifidobacteria are Gram-positive, anaerobic, rod-shaped lactic acid producing bacteria. The present *Bifidobacterium* species preferably have at least 95% identity of the 16 S rRNA sequence when compared to the type strain of the respective *Bifidobacterium* species, more preferably at least 97% identity as defined in handbooks on this subject for instance Sambrook, J., Fritsch, E. F., and Maniatis, T. (1989), Molecular Cloning, A Laboratory Manual, 2nd ed., Cold Spring Harbor (N.Y.) Laboratory Press. The Bifodobacteria preferably used are also described by Scardovi, V. Genus *Bifidobacterium*. p. 1418-p. 1434. In: Bergey's manual of systematic Bacteriology. Vol. 2. Sneath, P. H. A., N. S. Mair, M. E. Sharpe and J. G. Holt (ed.). Baltimore: Williams & Wilkins. 1986. 635 p. Preferably the bifidobacteria used in producing the present preparation is at least one *Bifidobacterium* selected from the group consisting of *B. breve, B. infantis, B. bifidum, B. catenulatum, B. adolescentis, B. thermophilum, B. gallicum, B. animalis* or *lactis, B. angulatum, B. pseudocatenulatum, B. thermacidophilum* and *B. longum* more preferably *B. breve, B. infantis, B. bifidum, B. catenulatum, B. longum*, more preferably *B. longum* and *B. breve*, even more preferably *B. breve*, most preferably *B. breve* I-2219 deposited at the CNCM in Paris, France. *B. breve* CNCM I-2219 was deposited under the Budapest Treaty at the Collection Nationale de Cultures de Microorganisms van Institute Pasteur, Paris, France on 31 May 1999 by Compagnie Gervais Danone. This strain was published in WO 2004/093899.

Preferably the composition also comprises a product obtained by incubating an aqueous substrate comprising at least one selected from the group consisting of milk, milk protein, whey, whey protein, whey protein hydrolysate, casein, casein hydrolysate and lactose, preferably the group of whey and lactose with streptococci and preferably subsequently inactivating and/or removing the streptococci. Streptococci are Gram-positive, anaerobic, coccoid-shaped lactic acid producing bacteria. The *Streptococcus* species preferably have at least 95% identity of the 16 S rRNA sequence when compared to the type strain of the respective *Streptococcus* species, more preferably at least 97% identity as defined in handbooks on this subject for instance Sambrook, J., Fritsch, E. F., and Maniatis, T. (1989), Molecular Cloning, A Laboratory Manual, 2nd ed., Cold Spring Harbor (N.Y.) Laboratory Press. Preferably production of a product obtained by incubating an aqueous substrate with streptococci and subsequently inactivating the streptococci is performed with *Streptococcus* species selected from the group consisting of *S. salivarius* and *S. thermophilus*, more preferably *S. thermophilus*, even more preferably strain *S. thermophilus* CNCM I-1620 or strain CNCM I-1470, most preferably strain CNCN I-1620. *S. thermophilus* CNCM I-1620 and I-1470 advantageously produces high amounts of beta-galactosidase. *S. thermophilus* CNCM I-1620 was deposited under the Budapest Treaty on 23 Aug. 1995 at Collection Nationale de Cultures de Microorganisms van Institute Pasteur, Paris, France by Compagnie Gervais Danone. *S. thermophilus* CNCM I-1470 was deposited under the Budapest Treaty on 25 Aug. 1994 at Collection Nationale de Cultures de Microorganisms van Institute Pasteur, Paris, France by Compagnie Gervais Danone. These strains were published in EP 778885.

Process Step a) Incubation the Aqueous Substrate

Step (a) is preferably performed by:

a1 inoculating bifidobacteria in the aqueous substrate in amount of between $1\times10^2$ to $1\times10^{11}$ cfu bifidobacteria/ml, said aqueous substrate having a pH of between 4 and 8, and comprising at least one selected from the group consisting of milk, whey, whey protein, whey protein hydrolysate, casein hydrolysate, and lactose, a2 incubating said bifidobacteria in said aqueous medium, under aerobic or anaerobic conditions and at a temperature of 20° C. to 50° C., for at least 2 h.

The aqueous substrate to be incubated with bifidobacteria comprises at least one, more preferably at least two, selected from the group consisting of milk, whey, whey protein, whey protein hydrolysate, casein hydrolysate, and lactose. Preferably the substrate does not comprise intact casein. It was found that less immunostimulatory substances were formed when the aqueous substrate comprised high amounts of intact casein. Therefore the aqueous substrate comprises preferably less than 25 g/l casein, more preferably less than 15 g/l, even more preferably less than 5 g/l, most preferably less than 1 g/l intact casein. The aqueous substrate therefore even more preferably comprises whey and/or whey protein and/or whey protein hydrolysate.

Milk can be whole milk, semi-skimmed milk and/or skimmed milk. Preferably skimmed milk is used. Whey can be sweet whey, acid whey or whey from which the casein has been removed for example by filtration or whey permeate. Preferably the whey is present in a concentration of 3 to 80 g dry weight per liter (l) aqueous substrate, more preferably 40 to 60 g per l. Preferably whey protein concentrate is used. Preferably whey protein hydrolysate is used and is present in an amount of 2 to 80 g dry weight per l aqueous substrate, more preferably 5 to 15 g/l. Preferably lactose is present in an amount of 5 to 50 g dry weight per l aqueous substrate, more preferably 1 to 30 g/l. Preferably the aqueous substrate comprises buffer salts in order to keep the pH within a desired range. Preferably sodium or potassium dihydrogen phosphate is used as buffer salt, preferably in an amount of 0.5 to 5 g/l, more preferably 1.5 to 3 g per l. Preferably the aqueous substrate comprises cysteine in amount of 0.1 to 0.5 g per l aqueous substrate, more preferably 0.2 to 0.4 g/l. The presence of cysteine results in low redox potential of the substrate which is advantageous for activity of lactic acid producing bacteria, particularly bifidobacteria. Preferably the aqueous substrate comprises yeast extract in an amount of 0.5 to 5 g/l aqueous substrate, more preferably 1.5 to 3 g/l. Yeast extract is a rich source of enzyme co-factors and growth factors for lactic acid producing bacteria. The presence of yeast extract will enhance the bioconversion and/or fermentation by bifidobacteria.

Preferably the aqueous substrate to be incubated comprises a high concentration of solids, preferably more than 20 wt. % solids based on volume, more preferably more than 40 wt. % solids. A high concentration is advantageous when performing the further processing steps, such as for example spray drying, centrifugation or filtration.

Suitably the aqueous substrate is pasteurised before the incubation step, in order to eliminate the presence of unwanted living bacteria. Suitably the product is pasteurised after incubation, in order to inactivate enzymes. Suitably the enzyme inactivation takes place at 75° C. for 1 min. Suitably the enzyme inactivation takes place at 75° C. for 3 min. Suitably the aqueous substrate is homogenised before and/or after the incubation step. Homogenisation results in a more stable product, especially in the presence of fat (lipids).

The inoculation density is preferably between $1\times10^2$ to $1\times10^{11}$, preferably between $1\times10^4$ to $1\times10^{10}$ cfu bifidobacteria per ml aqueous substrate, more preferably between $1\times10^7$ to $1\times10^9$ cfu bifidobacteria/ml aqueous substrate. Methods for obtaining a concentrated starter culture of bifidobacteria to be inoculated in the aqueous substrate are known in the art. The final bacteria density of bifidobacteria after incubation is preferably between $1\times10^3$ to $1\times10^{11}$, more preferably between $1\times10^4$ to $1\times10^9$ cfu/ml aqueous substrate.

The incubation with bifidobacteria is preferably performed at a temperature of approximately 20° C. to 50° C., more preferably 30° C. to 45° C., even more preferably approximately 37° C. to 42° C. The optimum temperature for growth and/or activity for bifidobacteria is between 37° C. and 42° C.

The incubation with bifidobacteria is preferably under anaerobic conditions, since the growth of bifidobacteria and the enzymatic activity of many enzymes of bifidobacteria are impaired under aerobic conditions. However acidification is not always desired. Thus, in one embodiment, the incubation step suitably takes place under aerobic conditions.

The incubation with bifidobacteria is preferably performed at a pH of 4 to 8, more preferably 5.6 to 7.5, even more preferably 6 to 7.5. This pH does not induce protein precipitation and/or an adverse taste, while at the same time bifidobacteria are able to interact with the aqueous substrate.

The incubation time is preferably at least 2 h, preferably between 4 and 48 h, more preferably between 6 and 24 h, even more preferably between 6 and 15 h. A sufficient long time enables the interaction between the bifidobacteria and the aqueous substrate and/or the production of cell fragments such as glycoproteins, glycolipids, peptidoglycan, lipoteichoic acid (LTA), lipoproteins, DNA and/or capsular polysaccharides to take place to a large extent, whereas the incubation time need not be unnecessarily long for economical reasons.

Methods of Inactivation and/or Physically Removal of Living Cells of Bifidobacteria In step (b) of the present process living cells bifidobacteria are after incubation in step a) preferably essentially all eliminated, for example by inactivation by heat treatment and/or physical removal. The cells are preferably inactivated by heat treatment. Preferably the bifidobacteria are heat killed after incubation step a). Preferable ways of heat killing are pasteurization, sterilization, ultra high temperature treatment, spray cooking and/or spray drying at temperatures bifidobacteria do not survive. The heat treatment is preferably performed at at least 50° C., more preferably at at least 65° C. The heat treatment is preferably performed for at least 5 minutes, more preferably for at least 10 minutes. The heat treatment is preferably performed for at least 5 minutes at at least 50° C., more preferably for at least 10 minutes at at least 65° C. The heat treatment is preferably performed for at least 1 minutes at at least 75° C., more preferably for at least 3 minutes at at least 75° C.

Preferably intact cells of bifidobacteria are removed from the incubated product by physical elimination such as filtration and/or centrifugation, for example centrifugation for 1 h at 3000 g, with the intact cells remaining in the pellet or retentate and the product obtained by incubating a milk and/or milk-derived substrate with bifidobacteria and subsequently inactivating the bifidobacteria cell fragments remaining in the supernatant and/or filtrate, respectively.

The heat inactivation and/or physical removal of living cells is such that the amount of living bifidobacteria after treatment is below the detection limit as used by conventional plating techniques known in the art. This detection limit is less than $10^4$ cfu living cells of bifidobacteria based on g dry weight composition, more preferably less than $10^3$ cfu/g. Preferably the heat inactivation and/or removal step is such that at least 90, more preferably at least 99% of the cells present in the incubated mixture after step a) is eliminated.

The requirement that living cells are inactivated has the advantage that, after production, the final nutritional composition can be pasteurised and/or sterilised, consequently reducing the chance of contamination with harmful microorganisms. So the present invention enables liquid, ready-to-use formula to be prepared and stored at room temperature. Furthermore, the dose of bioactive components received by each human subject can be more easily controlled, since no further growth in a liquid product occurs, nor growth in the intestinal tract of the human subject. The latter is a variable factor depending on the individual's intestinal environment, and thereby leads to variations in the extent of beneficial effects in individual subjects. Still a further advantage is that inactivated and/or removed bifidobacteria and streptococci no longer are able to breakdown and consume the non-digestible carbohydrates.

Additional advantages are that the nutritional composition can be stored more easily and with reduced costs, since no special precautions have to be taken to maintain the viability of bifidobacteria at an acceptable level. This is especially the case in products with a water activity above 0.3. Also no post-acidification occurs in stored products with a high water activity and/or in powdered nutritional compositions in the period after reconstitution with water and before consumption. Adverse effects relating to coagulation of proteins and adverse taste are avoided in this way.

Addition of Additional Components and Other Optional Process Steps

Optionally one or more of the following steps may follow the above process step b):

i) Ultrafiltrating the product after incubation through filtration membranes having a cut-off threshold between 100 and 300 kDa, so as to obtain a concentrated retentate. The membranes are preferably polyethersulfone membranes and filtration is preferably performed at a temperature below 60° C.

ii) Washing the concentrated retentate with water.

iii) Dehydrating the concentrated retentate, preferably by lyophilisation.

iv) Dissolving the dehydrated retentate in a buffer, preferably a Tris buffer with pH 6-8.

v) Performing gel exclusion chromatography of the retentate solution, on a column having an exclusion threshold of 600 kDa, preferably a Dextran or agarose column such as Superdex® 200.

vi) Recovery of the filtered or excluded fraction at the end of the chromatography vii) Desalting the product with a membrane with a cut-off of 10 kDa. Recovering the excluded fraction at the end of the chromatography.

These steps are preferably performed under sterile conditions. Additional ingredients that may be beneficial for obtaining the desired final nutritional composition may be added after process step a), preferably immediately prior to step b) or after process step b). Preferably these are added after step b). For an infant milk formula, ingredients such as skimmed milk, whey, lactose, vegetable fat, minerals, vitamins, as known in the art may be added.

Preferably, an aqueous substrate comprising whey, whey protein and/or whey protein hydrolysate, is pasteurized, cooled and incubated with one or more *Bifidobacterium* strains, preferably *B. breve* strain CNCM I-2219, upon which the incubated product is heat treated and stored. Optionally the incubated product is mixed with other components making up the nutritional composition. A fat component may or may not be included, but preferably a fat component is not yet included at this stage. Preferably, the mixture is preheated, and subsequently fat (also the term 'lipids' is used herein) is added in-line, homogenized, heat-treated and dried.

Another preferred method for preparing the incubated product of the present invention is disclosed in WO 01/01785, more particular in example 1 and 2. Another preferred method for preparing the incubated product of the present invention is described in WO 2004/093899, more particularly in example 1.

Preferably the final nutritional composition comprises from 5 to 100 wt. % based on dry weight of the preparation obtained by step b, more preferably from 5 to 99.5 wt. %, more preferably from 5 to 95 wt. %, even more preferably from 5 to 80 wt. %, even more preferably from 5 to 40 wt. %, most preferably from 10 to 40 wt. %. Preferably, the final nutritional composition comprises from 0.5 to 20 wt. % of a product obtained by step b per 100 ml, more preferably 0.5 to 14 wt. %, more preferably 1 to 10 wt. %, even more preferably 1 to 5 wt. % per 100 ml.

Preferably the present final nutritional composition comprises inactivated bifidobacteria and/or bacterial fragments derived from bifidobacteria obtained from more than $1\times10^3$ cfu bifidobacteria per g, based on dry weight of the final composition, more preferably more than $1\times10^4$ cfu, even more preferably more than $1\times10^5$ cfu. Preferably the inactivated bifidobacteria and/or bacterial fragments derived from bifidobacteria are obtained from less than $1\times10^{11}$ cfu bifidobacteria per g, based on dry weight of the final composition, more preferably less than $1\times10^{10}$ cfu, even more preferably less than $1\times10^9$ cfu. These numbers can be calculated by determining the amount of bifidobacteria in the mixture after incubation as in step a) and before step b), and subsequently taking into account how many gram of the present preparation is present in the final composition based on dry weight.

Additional ingredients that may be beneficial for obtaining the desired final nutritional composition may be added after process step a) or b). Preferably these are added after step a). For an infant milk formula, ingredients such as skimmed milk, whey, lactose, vegetable fat, minerals, vitamins, as known in the art may be added.

Preferably the process comprises the additional steps of d: incubating a substrate with *Streptococcus thermophilus*, preferably strain *S. thermophilus* CNCM I-1620 or strain CNCM I-1470, wherein the substrate is selected from the group consisting of milk, milk protein, whey, whey protein, whey protein hydrolysate, casein, casein hydrolysate, and lactose, to obtain an incubated mixture and e: inactivating the *S. thermophilus* by heating the incubated mixture of step e and/or removing *S. thermophilus* cells from the incubated mixture of step e by centrifugation and/or filtration. Step e and b are preferably performed simultaneously. Preferably intact cells of streptococci are removed from the incubated product by physical elimination such as filtration and/or centrifugation, for example centrifugation for 1 h at 3000 g, with the intact cells remaining in the pellet or retentate and the product obtained by incubating a milk and/or milk-derived substrate with streptococci and subsequently inactivating the streptococcal cell fragments remaining in the supernatant and/or filtrate, respectively.

The heat inactivation and/or physical removal of living cells is such that the amount of living streptococci after treatment is below the detection limit as used by conventional plating techniques known in the art. This detection limit is less than $10^4$ cfu living cells of streptococci based on g dry weight composition, more preferably less than $10^3$ cfu/g. Hence, preferably in one embodiment according to the invention the preparation after step e comprises less than $10^3$ cfu living streptococci per g dry weight of the preparation. Preferably the heat inactivation and/or removal step is such that at least 90, more preferably at least 99% of the cells present in the incubated mixture after step d) is eliminated.

Another preferred method for preparing the incubated product with *S. thermophilus* strains of the present invention is disclosed in EP 0778885, more particular in example 5 and 6. Another preferred method for preparing the incubated product with *S. thermophilus* strains of the present invention is disclosed in FR2723960 examples 2 to 6.

Preferably, an aqueous substrate comprising whey, whey protein and/or whey protein hydrolysate, is pasteurized, cooled and incubated with one or more *Bifidobacterium* strains, preferably *B. breve* strain CNCM I-2219, upon which the incubated product is heat treated and stored. Preferably a second aqueous substrate comprising whey and/or lactose is incubated with *S. thermophilus*, preferably strain CNCM I-1620 or strain CNCM I-1470. Subsequently, the two incubated products are preferably mixed together and mixed with other components making up the nutritional composition. A fat component may or may not be included, but preferably a fat component is not yet included at this stage. Preferably, the mixture is preheated, and subsequently fat (also the term 'lipids' is used herein) is added in-line, homogenized, heat-treated and dried.

The incubation step d may be performed simultaneously with the incubation step with bifidobacteria in step a. Preferably the incubation with *S. thermophilus* is performed in a separate process step from the incubation with bifidobacteria. Separate incubation allows optimum conditions for each of the different bacteria and/or prevents unwanted interference of the different bacteria with the release of immunostimulatory components. Preferably the incubated mixture obtained after incubation of the substrate with streptococci is added to the mixture obtained in step a, step b, or step c, more preferably after step a). An improved effect on delayed hyper hypersensitivity response is observed when the present composition also comprised a mixture obtained after incubation with *S. thermophilus*. Thus in one embodiment the process according to the invention comprises the further step of:

f: combining the incubated mixture obtained in step d or e, preferably step d, with the incubated mixture obtained in step a, b, or c, preferably in step a. In one embodiment the incubated mixture obtained in step d is combined with the incubated mixture obtained in step a and steps b and e are performed simultaneously.

Preferably the final nutritional composition comprises from 2 to 94.5% based on dry weight of the preparation obtained by step d, more preferably from 5 to 80 wt. %, even more preferably from 5 to 40 wt. %. Preferably, the final nutritional composition comprises from 0.2 to 20 wt. % of a product obtained by step d per 100 ml, more preferably 0.5 to 14 wt. %, more preferably 1 to 10 wt. %, even more preferably 1 to 5 wt. % per 100 ml.

Non-Digestible Carbohydrates

The preparation obtained by the present process comprises at least two different non-digestible carbohydrates. These non-digestible carbohydrates are added in process step c). The non-digestible carbohydrates advantageously stimulate the immune system. This stimulation may occur via an improvement of the intestinal microbiota and/or via a direct effect on the immune system. The presence of two different non-digestible carbohydrates synergistically improves the intestinal flora and/or synergistically stimulates the immune system.

The presence of both two non-digestible carbohydrates and a product obtained by incubating an aqueous substrate with bifidobacteria and subsequently inactivating and/or removing the bifidobacteria acts synergistically on the immune response. The combination unexpectedly synergistically results in a higher Th1 response, a lower Th2 response and/or an increased Th1/Th2 response ratio. The combination synergistically increases vaccination response, synergistically improves allergic reaction and/or increases resistance against infections. The synergistic effect between these two compounds was unexpected and cannot be explained by a symbiotic effect, wherein the non-digestible carbohydrates are specifically stimulating the growth of the beneficial micro-organisms present in the same preparation, since no living bifidobacteria are present in the incubated milk and/or milk-derived product.

The term "oligosaccharide" as used in the present invention refers to carbohydrates with a degree of polymerization (DP) of 2 to 250, preferably a DP 2 to 100, more preferably 2 to 60, even more preferably 2 to 10. If the oligosaccharide with a DP of 2 to 100 is included in the present preparation, this includes compositions which contain oligosaccharides with a DP between 2 and 5, a DP between 50 and 70 and a DP of 7 to 60. The term "non-digestible carbohydrate" as used in the present invention refers to carbohydrates which are not digested in the intestine by the action of acids or digestive enzymes present in the human upper digestive tract (small intestine and stomach) but which are preferably fermented by the human intestinal microbiota. For example, sucrose, lactose, maltose and maltodextrins are considered digestible.

Preferably the present non-digestible carbohydrate is soluble. The term "soluble" as used herein, when having reference to a carbohydrate, means that the carbohydrate is soluble according to the method described by L. Prosky et al., J. Assoc. Off. Anal. Chem. 71, 1017-1023 (1988).

Different non-digestible carbohydrates in the present invention relates to non-digestible carbohydrates differing in monosaccharide unit composition, or differing in degree of polymerization (DP) or both. Two non-digestible carbohydrates differ in monosaccharide composition when there is at least 30 mol % difference, more preferably at least 50 mol % difference in monosaccharide composition based on total mol monosaccharide units. For instance galacto-oligosaccharides with an average composition of Glu-Gal$_3$ and fructo-oligosaccharides with an average composition of Glu-Fru$_3$ differ for 75 mol %. Two non-digestible carbohydrates differ in DP if the average DP of the two carbohydrates differs more than 5 monosaccharide units, preferably more than 10 units, even more preferably more than 15 units. For example hydrolysed inulin with an average DP of 4 and long chain inulin with an average DP of 25 have a difference in DP of 21 units.

The non-digestible carbohydrates are at least one, more preferably at least two, selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the present preparation comprises fructo-oligosaccharides, galacto-oligosaccharides and/or galacturonic acid oligosaccharides, more preferably galacto-oligosaccharides, most preferably beta-galacto-oligosaccharides. The group of fructo-oligosaccharides includes inulin, the group of galacto-oligosaccharides includes transgalacto-oligosaccharides or beta-galacto-oligosaccharides, the group of gluco-oligosaccharides includes gentio-, nigero- and cyclodextrin-oligosaccharides and polydextrose, the group of arabinogalacto-oligosaccharides includes gum acacia, and the group of galactomanno-oligosaccharides includes partially hydrolysed guar gum.

For further improvement, the present non-digestible carbohydrates preferably have a relatively high content of short chain oligosaccharides, as these strongly stimulate the growth of bifidobacteria. Hence, preferably at least 10 wt. % of the non-digestible carbohydrates in the present preparation has a DP of 2 to 5 (i.e. 2, 3, 4, and/or 5) and at least 5 wt. % has a DP of 10 to 60. Preferably at least 50 wt. %, more preferably at least 75 wt. % of the non-digestible carbohydrates has a DP of 2 to 9 (i.e. 2, 3, 4, 5, 6, 7, 8, and/or 9).

More preferably the preparation obtained by the present process comprises galacto-oligosaccharides. The galacto-oligosaccharides are preferably selected from the group consisting of beta-galacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present preparation comprises beta-galacto-oligosaccharides. Beta-galacto-oligosaccharides as used in the present invention refers to oligosaccharides composed of over 50%, preferably over 65% galactose units based on monomeric subunits, with a degree of polymerization (DP) of 2 to 20, in which at least 50%, more preferably at least 75%, even more preferably at least 90%, of the galactose units are linked together via a beta-glycosidic linkage, preferably a beta-1,4 glycosidic linkage. Beta-linkages are also predominant in human milk oligosaccharides. The average DP is preferably in the range of 3 to 6. A glucose unit may be present at the reducing end of the chain of galactose units. Beta-galacto-oligosaccharides are sometimes also referred to as transgalacto-oligosaccharides (TOS). A suitable source of beta-galacto-oligosaccharides is Vivinal® GOS (commercially available from Borculo Domo Ingredients, Zwolle, Netherlands). Other suitable sources are Oligomate (Yakult), Cupoligo, (Nissin) and Bi2muno (Classado). Beta-galacto-oligosaccharides were found to stimulate the growth of lactic acid producing bacteria, especially bifidobacteria.

Preferably the preparation obtained by the present process comprises fructo-oligosaccharides. Fructo-oligosaccharides as used in the present invention refers to carbohydrates composed of over 50%, preferably over 65% fructose units based on monomeric subunits, in which at least 50%, more preferably at least 75%, even more preferably at least 90%, of the fructose units are linked together via a beta-glycosidic linkage, preferably a beta-2,1 glycosidic linkage. A glucose unit may be present at the reducing end of the chain of fructose units. Preferably the fructo-oligosaccharide has a DP or average DP in the range of 2 to 250, more preferably 2 to 100, even more preferably 10 to 60. Fructo-oligosaccaride comprises levan, hydrolysed levan, inulin, hydrolysed inulin, and synthesised fructo-oligosaccharides. Preferably the preparation comprises short chain fructo-oligosaccharides with an average degree of polymerization (DP) of 3 to 6, more preferably hydrolysed inulin or synthetic fructo-oligosaccharide. Preferably the preparation comprises long chain fructo-oligosaccharides with an average DP above 20. Preferably the preparation comprises both short chain and long chain fructo-oligosaccharides. Fructo-oligosaccharide suitable for use in the process of the invention is also readily commercially available, e.g. RaftilineHP (Orafti).

More preferably the preparation obtained by the process according to the invention comprises a combination of galacto-oligosaccharides and fructo-oligosaccharides, more preferably long chain fructo-oligosaccharides. Such a mixture synergistically stimulates the growth of a healthy intestinal microbiota, particularly bifidobacteria.

The preparation obtained by the process according to the invention preferably comprises uronic acid oligosaccharides, more preferably mannonuric acid and/or galacturonic acid oligosaccharides, even more preferably galacturonic acid. The term uronic acid oligosaccharide as used in the present invention refers to an oligosaccharide wherein at least 50% of the monosaccharide units present in the oligosaccharide is uronic acid. The term galacturonic acid oligosaccharide as used in the present invention refers to an oligosaccharide wherein at least 50% of the monosaccharide units present in the oligosaccharide is galacturonic acid. The galacturonic acid oligosaccharides used in the invention are preferably prepared from degradation of pectin, pectate, and/or polygalacturonic acid Preferably the degraded pectin is prepared by hydrolysis and/or beta-elimination of fruit and/or vegetable pectins, more preferably apple, citrus and/or sugar beet pectin, even more preferably apple, citrus and/or sugar beet pectin degraded by at least one lyase. In a preferred embodiment, at least one of the terminal galacturonic acid units of the galacturonic acid oligosaccharide has a double bond. The double bond effectively protects against attachment of pathogenic bacteria to intestinal epithelial cells. Preferably one of the terminal galacturonic acid units comprises a $C_4$-$C_5$ double bond. The galacturonic acid oligosaccharide can be derivatised. The galacturonic acid oligosaccharide may be methoxylated and/or amidated. Preferably the galacturonic acid oligosaccharides are characterised by a degree of methoxylation above 20%, preferably above 50% even more preferably above 70%. Uronic acid oligosaccharides advantageously reduce the adhesion of pathogenic micro-organisms to the intestinal epithelial cells. Furthermore, uronic acid oligosaccharides stimulate the immune system by increasing the Th1 response.

Thus, in one embodiment the preparation obtained by the process according to the invention and for use according to the present invention preferably comprises at least beta-galacto-oligosaccharides. In one embodiment the preparation obtained by the process according to the invention and for use according to the present invention preferably comprises at least short chain fructo-oligosaccharides and/or long chain fructo-oligosaccharides, preferably long chain fructo-oligosaccharides. In one embodiment the preparation obtained by the process according to the invention and for use according to the present invention preferably comprises at least uronic acid oligosaccharides. In one embodiment the preparation for use according to the present invention preferably comprises at least beta-galacto-oligosaccharides and at least short chain fructo-oligosaccharides or long chain fructo-oligosaccharides or both. In one embodiment the preparation for use according to the present invention preferably comprises at least beta-galacto-oligosaccharides and at least uronic acid oligosaccharides. In one embodiment the preparation for use according to the present invention preferably comprises at least short chain fructo-oligosaccharides and uronic acid oligosaccharides or long chain fructo-oligosaccharides and uronic acid oligosaccharides. In one embodiment the preparation for use according to the present invention preferably comprises at least beta-galacto-oligosaccharides and short chain fructo-oligosaccharides and uronic acid oligosaccharides or at least beta-galacto-oligosaccharides and long chain fructo-oligosaccharides and uronic acid oligosaccharides. A combination of uronic acid oligosaccharides together with a combination of galacto-oligosaccharides and/or fructo-oligosaccharides results in a higher Th1 response than the uronic acid oligosaccharides or galactose and/or fructo-oligosaccharides alone.

Preferably the weight ratio between the mixture of two different non-digestible carbohydrates, preferably beta-galacto-oligosaccharides and fructo-oligosaccharide, is between 20 and 0.05, more preferably between 20 and 1. Beta-galacto-oligosaccharides are more reminiscent to the human milk oligosaccharides. Preferably the present preparation comprises beta-galacto-oligosaccharides with a DP of 2-10 and/or fructo-oligosaccharides with a DP of 2-60. This combination was found to synergistically increase bifidobacteria and lactobacilli. The presence of these three non-digestible oligosaccharides even further stimulates the bifidobacteria. The weight ratio transgalacto-oligosaccharide:fructo-oligosaccharide:uronic acid oligosaccharide is preferably (20 to 2):1:(1 to 20), more preferably (12 to 7):1:(1 to 3).

Preferably, the final nutritional composition consisting of or comprising the preparation obtained by the process according to the invention comprises 80 mg to 2 g non-digestible carbohydrates per 100 ml, more preferably 150 mg to 1.50 g, even more preferably 300 mg to 1 g. Based on dry weight, the nutritional composition preferably comprises 0.25 wt. % to 20 wt. %, more preferably 0.5 wt. % to 10 wt. %, even more preferably 1.5 wt. % to 7.5 wt. % non-digestible carbohydrates. A lower amount of non-digestible carbohydrate will be less effective in stimulating the immune system and/or beneficial bacteria in the microbiota, whereas a too high amount will result in side-effects of bloating and abdominal discomfort.

The two different non-digestible carbohydrates are added (i.e. step c) after step a) preferably immediately prior to step b) or after step b), preferably step c) is conducted after step b), preferably step c) is conducted after step e), i.e. after inactivation by heat treatment and/or removal of the bifidobacteria and optionally S. thermophilus.

Preferably the preparation obtained by the process according to the invention comprises an aqueous substrate comprising at least one of the group selected from milk, milk protein, whey, whey protein, whey protein hydrolysate and lactose incubated with B. breve, more preferably strain CNCM I-2219, and at least one, preferably two non-digestible carbohydrates from the group consisting of galacto-oligosaccharides and fructo-oligosaccharides.

In one aspect the present invention concerns the present process, wherein in step c only one non-digestible carbohydrate is added. It is particularly advantageous that the only one non digestible carbohydrate is fructo-oligosaccharide.

In one aspect, the invention concerns a preparation obtainable by the process according to the present invention as described above. In one embodiment the final nutritional composition consisting of or comprising the preparation obtained by the present process comprises 0.5 to 10 g non-digestible carbohydrate as defined above per 100 g dry weight of the composition. In one embodiment the final nutritional composition consisting of or comprising the preparation obtained by the present process has a viscosity of 1 to 60 mPa·s at a shear rate of $100\ s^{-1}$ at 20° C.

Preferably the above process comprises a drying step. Drying steps are known in the art. A suitable drying step is spray drying. Preferably the drying step is performed in such a way that the dried product is a powder comprising less than 10 wt. % water, more preferably less than 5 wt. %. Preferably the drying step is performed after step c. Alternatively, the drying step may be performed after step b and/or after step e, after which the non-digestible oligosaccharides are dry blended in the product.

Nutrition

It was found that the present preparation can be advantageously applied in food, such as baby food and clinical food. The present preparation or composition comprising the present preparation is preferably enterally administered, more preferably orally. Preferably the composition is a complete nutrition.

Preferably the nutrition is suitable for administration to infants. More preferably the present nutritional composition is an infant or follow on formula. The present composition can be advantageously applied as a complete nutrition for infants.

Preferably the present composition is an infant nutrition comprising based on dry weight of the infant nutrition i) from 0.5 to 10 wt. % of the sum of galacto-oligosaccharides and fructo-oligosaccharides, and ii) from 5 to 99.5 wt. % of the preparation obtained after step b according to the present process, wherein the bifidobacteria in step a belong to the species B. breve, preferably strain B. breve CNCM I-2219 iii) and optionally 2 to 94.5 wt. % of the preparation obtained after step e.

Such nutrition preferably comprises lipid, protein and carbohydrate and is preferably administered in liquid form. The term "liquid food" as used in the present invention includes dry food (e. g. powders) which are accompanied with instructions as to admix said dry food mixture with a suitable liquid (e. g. water).

Hence, the nutritional composition of the present invention preferably comprises between 5 and 60% lipids based on total of calories, between 5 and 60% protein based on total calories, between 15 and 90% digestible carbohydrate based on total calories. Preferably the present nutritional composition comprises between 5 and 30% lipid based on total calories, between 15 and 40% protein based on total calories and between 25 and 75% digestible carbohydrate based on total calories when intended for adult human subjects. Preferably the present nutritional composition comprises between 30 and 60% lipid based on total calories, between 5 and 15% protein based on total calories and between 25 and 75% digestible carbohydrate based on total calories, more preferably 35 to 50% lipids based on total calories, 7.5 to 12.5% proteins based on total calories, and 40 to 55% digestible carbohydrate based on total calories when intended for infants. For calculation of the % protein based on total calories, the total of calories provided by proteins, peptides and amino acids needs to be taken into account.

Preferably the lipids comprise vegetable oils. The vegetable lipid is preferably at least one selected from the group consisting of soy oil, palm oil, coconut oil, safflower oil, sunflower oil, corn oil, canola oil and lecithins. Preferably a combination of vegetable lipids and at least one oil selected from the group consisting of fish oil and omega-3 containing vegetable, algae or bacterial oil is used. In a preferred embodiment, the present method further comprises the administration of long-chain polyunsaturated acid (LC-PUFA). As it is believed that these act on the immune system via a mechanism different from the non-digestible carbohydrates and the product obtained by incubating a milk and/or milk-derived substrate with bifidobacteria and subsequently inactivating the bifidobacteria, the combination of the present invention with the LC-PUFA is deemed to act synergistically.

The nutritional composition of the present invention preferably comprises between 5 and 60% lipids based on total of calories, preferably between 5 and 30% lipid based on total calories when intended for adults, preferably between 30 and 60% lipid based on total calories, more preferably 35 to 50% lipids based on total calories, when intended for infants.

The proteins used in the nutritional preparation are preferably selected from the group of non-human animal proteins (such as milk proteins, meat proteins and egg proteins), vegetable proteins (such as soy protein, wheat protein, rice protein, and pea protein), hydrolysates thereof, free amino acids and mixtures of proteins, hydrolysates and free amino acids. Cow milk proteins such as casein and whey proteins are particularly preferred. As the present composition is suitably used to reduce the allergic reactions, especially in infants, the protein of is preferably selected from the group consisting of hydrolyzed milk protein. Preferably the present composition comprises hydrolyzed casein and/or hydrolyzed whey protein, hydrolyzed vegetable protein and/or free amino acids, most preferably hydrolyzed whey protein. The use of these proteins further reduced the allergic reactions. The use of these hydrolysed proteins advantageously improves the absorption of the dietary protein component. This is especially advantageous for infants and for subjects suffering from a disorder.

The nutritional composition of the present invention preferably comprises between 5 and 60% protein based on total calories, preferably between 15 and 40% protein based on total calories when intended for adult human subjects, and preferably between 5 and 15% protein based on total calories and more preferably 7.5 to 12.5% proteins based on total calories, calories when intended for infants. For calculation of the % protein based on total calories, the total of calories provided by proteins, peptides and amino acids needs to be taken into account.

A source of digestible carbohydrate may be added to the nutritional formula. Any suitable (source of) digestible carbohydrate may be used, for example sucrose, lactose, glucose, fructose, corn syrup solids, and maltodextrins, and mixtures thereof. Hence, the nutritional composition of the present invention preferably comprises between 15 and 90% carbohydrate based on total calories, more preferable between 25 and 75% carbohydrate based on total calories, more between 40 to 55% carbohydrate based on total calories.

The nutritional composition of the present invention is preferably is in liquid form. It preferably has a limited viscosity. It was found that the present process provides a liquid nutrition with sufficiently low viscosity so it can be applied as e. g. liquid baby foods and liquid clinical food which can be fed through a teat, a tube or a straw, while retaining the low viscosity. In a preferred embodiment, the present composition has a viscosity below 600 mPa·s, preferably below 250 mPas, more preferably below 60 mPa·s, even more preferably below 35 mPa·s, most preferably below 6 mPa·s, at a shear rate of $100\ s^{-1}$ at 20° C. Whenever the term viscosity used in the present document, this refers to the physical parameter which is determined according to the following method: The viscosity may be determined using a Carri-Med CSL rheometer. The used geometry is of conical shape (6 cm 2 deg acrylic cone) and the gap between plate and geometry is set on 55 um. A linear continuous ramp shear rate is used from 0 to $150\ s^{-1}$ in 20 seconds. It is noted that a composition in powder form with the instruction to prepare an aqueous solution, e.g. by adding water in a certain ratio and which then results in a viscosity as specified is also encompassed by the invention.

Stool irregularities (e. g. hard stools, insufficient stool volume, diarrhoea) is a major problem in many babies and ill subjects that receive liquid foods. It was found that stool problems may be reduced by administering the present preparation in liquid food which has an osmolality between 50 and 500 mOsm/kg, more preferably between 100 and 400 mOsm/kg.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml. When used as an infant formula the caloric density is most preferably between 0.6 and 0.8 kcal/ml.

Application

The present preparation obtained by the present process was found to synergistically stimulate the immune-system. In particularly the Th2 response was lowered, and/or the Th1 response was increased. The effect of the combination of these two components is higher than the sum of the effects of the single components.

The present preparation can advantageously be used in the treatment and/or prevention of a disease, and thus the invention concerns a method for the treatment and/or prevention of a disease in a mammal, said method comprising administering the present preparation to the mammal. In other words, the invention also concerns the use of a preparation according to the present invention for the manufacture of a composition, preferably a nutritional composition, for the treatment and/or prevention of a disease. In other words the invention concerns a preparation or nutritional composition comprising a preparation according to the present invention for use in the treatment and/or prevention of a disease. Preferably the mammal is a human, even more preferably a human infant. Thus the invention also concerns the use of a preparation according to the present invention for the manufacture of a composition, preferably a nutritional preparation, for the treatment and/or prevention of a disease in an infant. Or in other words the invention concerns a preparation or nutritional composition comprising a preparation according to the present invention for use in the treatment and/or prevention of a disease in an infant.

In the context of this invention, an infant is in the age of 0 to 6 years, preferably in the age of 0 to 4 years, preferably in the age of 0 to 2 years, preferably in the age of 0 to 1 year.

Also the invention concerns a method for providing nutrition to an infant, said method comprising administering the present preparation or nutritional composition to the infant. In other words, the invention also concerns the use of a preparation according to the present invention for the manufacture of a nutritional composition for providing nutrition to an infant. In other words the invention concerns a preparation or nutritional composition comprising a preparation according to the present invention for use in providing nutrition to an infant.

The present preparation can advantageously be used to increase the Th1 response, decrease the Th2 response, restore imbalance in the Th1/Th2 responses, maintain a favorable Th1/Th2 balance and/or for the treatment and prevention of disorders which are associated with an Th1/Th2 imbalance. Hence, compositions which are advertised to e. g. simulate maturation of the immune system, enhance the resistance to pathogens by enhancing the immune system and/or support the immune system are part of the present invention. In a further aspect, the present invention provides a method for the treatment and/or prevention of an immune system related disorder, said method comprising administering to said mammal a composition comprising a therapeutically effective amount of the present preparation. In a further aspect, the present invention provides a method of enhancing the immune response in a mammal said method comprising administering to the mammal the present preparation.

The immune system of newborn human infants is characterized by an excess of Th2 response. During maturation of the immune system, the Th1 response increases and the Th1/Th2 balance shifts to values observed for healthy adults. Hence, the present preparation is especially advantageous for human infants. The present invention supports the maturation of the immune system in infants. In a further embodiment, the method of the invention relates to the administration of the present preparation to humans in the age of 0 to 6 years, preferably in the age of 0 to 4 years, preferably in the age of 0 to 2 years, more preferably in the age of 0 to 1 year.

In a preferred embodiment the present method relates to the stimulation of the maturation of the immune system in human subjects in the age of 0-6 years, preferably in the age of 0 to 4 years, preferably in the age of 0 to 2 years, more preferably in the age of 0 to 1 year.

An excessive Th2 response leads to extreme sensitivity towards foreign components which should not lead to any immunological reaction, e. g. allergies and related diseases such as atopic dermatitis, asthma, food allergy, allergic rhinitis (e. g. pollen allergy), dust mite allergy and other forms of hypersensitivity like systemic anaphylaxis and acute urticaria. Hence, the present preparation is especially advantageous for treatment and/or prevention of a disorder selected from the group consisting of allergy, food allergy, atopic dermatitis, asthma, allergic rhinitis, dust mite allergy and urticaria. The present invention decreases the Th2 response.

An increase in Th1 response leads to an increase in the response against pathogenic bacteria and/or viruses. Hence, the present preparation is suitable for the treatment and/or prevention of infections. The present preparation can be advantageously used for the treatment and/or prevention of intestinal infections, systemic infections and/or respiratory tract infections.

It was also found that the present preparation can suitably be used to support vaccination processes, e. g. enhance the effects of a vaccination process. The present preparation is suitable for supporting vaccination response before, during and/or after vaccination. Particularly the effects of vaccinations for diptheria-tetanus, pertussis, polio vaccine, measles/mumps/rubella, pneumococcal conjugate, haemophilus B conjugate, hepatitis B, hepatitis A, varicella, influenza can suitably be enhanced. Hence, the present preparations are advantageously used in the treatment and/or prevention of infections, and/or for use in enhancement of vaccination response.

In the context of the present invention, 'prevention' of a disease or certain disorder also means 'treatment of a person at risk' of a disease or certain disorder.

Hence, the present preparation is advantageous for humans subjects suffering from immune deficiencies, in particular elderly humans suffering from immunosenescence, humans suffering from AIDS or being infected with the Human Immunodeficiency Virus, and cancer patients, more particular cancer patients that are or have been subjected to chemotherapy, radiation and cancer patients that are cachectic, patients suffering from chronic obstructive pulmonary disease and/or patients suffering from diabetes.

Example 1: Preparation of an Incubated Mixture Using *B. breve*

Pasteurized skimmed cow's milk was concentrated by evaporation to 43 wt. % dry matter based on weight of the skimmed cow's milk. The concentrate was cooled to 37° C., was then inoculated with 10% (v/w) *B. breve* CNCM I-2219 culture comprising $3 \times 10^9$ cfu per ml. This inoculum was prepared as described below. The initial pH was between 6-6.1. After incubating for 8 h at 37° C., in a tank with periodic stirring for 10 minutes every 2 hours, the pH stayed between 6-6.1 and the *B. breve* population was $10^6$ bacteria/ml (step (a)). The concentrate was pasteurized (step b) and subsequently spray-dried and called BbC50cf.

The inoculum was prepared as follows: A starter culture in the form of concentrated pellets was added to pasteurized skimmed milk and incubated for 8 h at 37° C. under anaerobic conditions. During the process the number of *B. breve* cells increased to about $3 \times 10^9$ cfu per ml and an acidification from about pH 6.7 to a pH of between 4.5 and 5.0 occurred. Suitably cysteine in amount of 0.1 to 0.5 g per 1 and/or yeast extract in an amount of 0.5 to 5 g/l aqueous substrate, was present.

Example 2: Preparation of an Incubated Mixture Using *S. thermophilus*

A pre-warmed inoculum was prepared from *S. thermophilus* CNCM I-1620 culture by maintaining a frozen inoculum for about 7 h at about 40° C. Pasteurized lactose solution (between 350 and 450 g/l) was cooled to about 45 and 55° C., and then inoculated with about 10% (v/w) *S. thermophilus* CNCM I-1620 pre-warmed inoculum comprising about $3 \times 10^9$ cfu per ml. The initial pH was about pH 6. After incubating for about 7 h at about 50° C., in a tank with periodic stirring for 10 minutes every 2 hours, the pH was kept constant between 6-8 and the *S. thermophilus* population was about $10^6$ bacteria/ml (step (d)). The concentrate was pasteurized (step e) and subsequently spray-dried and called St065cf.

Example 3: Synergistic Effect of the Incubated Mixture and Non-Digestible Carbohydrates on Th1 Response Increase Methods:

The effect of diets comprising (a) BbC50cf prepared according to example 1; (b) a combination of galacto-oligosaccharides (Elixor) and fructo-oligosaccharides (Raftilin HP); and (c) a combination of (a) and (b), i.e. comprising step c) of the present process, were tested in a mouse model wherein a response to an antigen is measured by a delayed-type hypersensitivity (DTH) response. This DTH response in the ears after local challenge with an antigen present in a vaccine is a measure of Th1 cell proliferation. During response to infection and/or vaccination Th1 cells proliferate in response to the challenge with the antigen. These Th1 cells infiltrate the ear when the ear is subsequently challenged with the antigen and cause swelling. Infiltration with the Th1 cells in the ear takes about 24 h and the swelling is therefore delayed. The more Th1 cells proliferated during initial vaccination and/or infection, the more DTH upon challenging with the antigen is observed.

The BbC50cf was lyophilized and used in the mouse diet in a final concentration of 3 wt. %. Non-digestible oligosaccharide mixture (GF) containing transgalacto-oligosaccharides (GOS) (source Vivinal-GOS (Borculo Domo Ingredients, Netherlands)) and fructo-oligosaccharide (FPS) (source RaftilineHP, Orafti, Tiense, Belgium) were used in a weight ratio GOS:FPS of 9:1. Diets containing 1 wt. % GF based on total weight of the mouse diet were tested. The effects of a combination of non-digestible oligosaccharides and *B. breve* incubated mixture (GF plus BbC50cf) was tested in a diet containing 1 wt. % GF and 3 wt. % BbC50cf based on total weight of the diet.

Female, 6 weeks old C57B1/6 mice (Harlan Nederland BV, Horst, the Netherlands) were group-housed under a regular 12 hours light/dark regime. Group size was 10 animals per group and 3 animals in the negative control groups. The animals were given semi-synthetic diets (Research Diet Services, Wijk bij Duurstede, the Netherlands). Control diets were made to the AIN93G specifications (Reeves et al (1993) J Nutrition 123 (11): 1923-31), oligosaccharide supplemented diets were based on these specifications.

Vaccinations were started after a period of 20 days of adaptation to the new housing and diets. At day 0, a blood sample was collected prior to vaccination. At day 1, the first vaccination was administered subcutaneously. After three weeks, a booster vaccination was given (day 22). Nine days after booster injection (day 31), basal ear thickness was measured with a Digimatic outside micrometer (Mitutoyo, Veenendaal, the Netherlands) and a delayed-type hypersensitivity (DTH) response was induced by injecting antigen solution i. c. (intracutaneous) in the mouse ear pinnae. 24 h thereafter (day 32), the DTH response was measured, a blood sample was taken and the mice were sacrificed. This is the ear thickness after 24 h subtracted with the ear thickness at t=0.

The vaccinations consisted of a 100 µl i. c. (intracutaneous) injection of a 1:1 mix of antigen solution and Stimune adjuvant (Specol, Cedi-diagnostics BV, Lelystad, the Netherlands). The antigen solution was a 1:100 dilution of Influvac 2002/2003 (Solvay Pharmaceuticals, Weesp, the Netherlands) in PBS. Influvac is a trivalent protein vaccine, containing 3×3011 g/ml haemagglutinin of three different influenza strains. For the DTH responses, mice were i. c. injected with 25 µl dialysed Influvac in both ears as a DTH challenge.

Results:

The diets containing dosages of 1 wt. % GF or 3 wt. % BbC50cf both induced a small non-statistically significant increase in the DTH response. The combination of 1 wt. % GF and 3 wt. % BbC50cf induced a statistically significant increase of 89% in the DTH response (see Table 1). As the effect is significantly higher than the DTH responses from diets containing the oligosaccharides alone, and also much higher than based on the additive effect of GF and BbC50cf, which can be calculated to be 49% increase of DTH, these results are indicative for the synergistic effect provided by the administration of non-digestible oligosaccharides and BbC50cf on Th1 response increase. The observed effect is indicative for the advantageous use of a combination of at least two different non-digestible carbohydrates and a product obtained by incubating an aqueous substrate with bifidobacteria, subsequently heating the incubated mixture and/or removing the bifidobacteria cells by centrifugation and/or centrifugation in the present uses.

TABLE 1

| Group: | DTH response | | |
|---|---|---|---|
| | Mean DTH µm (S.E.) | Δ DTH µm | Relative DTH |
| Sham | −1.7 (4.6) | 0 | 0 |
| Placebo | 67.6 (14.9) | 69.3 | 1.00 |
| GF | 73.55 (8.6) | 75.25 | 1.09 |
| BbC50cf | 95.55 (5.5) | 97.25 | 1.40 |
| GF + BbC50cf | 129.4* (17.1) | 131.1 | 1.89 |
| GF + BbC50cf theoretically | 101.50 | 103.2 | 1.49 |

*significantly different from control (P < 0.01).

The results of this experiment are an indication that the present invention can advantageously be used for support in vaccination response. The results of this experiment are also an indication that it can advantageously be used in subjects with a low Th1 response, in particular infants. The results of this experiment are also an indication that it can advantageously be used in subjects with a low Th1 response, in particular elderly suffering or at risk for suffering from immunosenescence, HIV patients, AIDS patients and/or cancer patients that are or have been subjected to chemotherapy and/or radiation or that are cachectic, patients suffering from COPD and/or patients suffering from diabetes. This model is indicative for basic immunological changes, which can be beneficial in all disorders with malfunctioning immune system. It is known that infants, elderly, HIV infected, cancer patients, COPD patients and/or diabetes patients have an immune system that does not function at full capacity. For all the above is an additional help possibly beneficial.

Example 4: Improved Effect of the Incubated Mixtures Obtained with *B. breve* and *S. thermophilus* and Non-Digestible Carbohydrates on Th1 Response Increase Methods:

The effect of diets comprising (a) BbC50cf (3 wt. %) prepared according to example 1 and a combination of galacto-oligosaccharides (Elixor) and fructo-oligosaccharides (Raftilin HP); (b) BbC50cf (3 wt. %) prepared according to example 1 and St065cf (3 wt. %) prepared according to example 2 and (c) a combination of BbC50 (3 wt. %), St065f (3 wt. %) and galacto-oligosaccharides and fructo-oligosaccharides were tested in a separate experiment, using the same mouse model as in example 3.

Galacto-oligosaccharides (Elixor) and fructo-oligosaccharides (Raftilin HP) (GF) were present in a 9:1 weight ratio and in 1 wt. % based on total diet.

Results:

The diets containing a combination of 1 wt. % GF and 3 wt. % BbC50cf induced a statistically significant increase of 100% in the DTH response (see Table 2).

The combination of BbC50cf and St065cf also induced a statistically significant increase of 112 in the DTH response.

Surprisingly a combination of all three ingredients showed the highest response increase of 192%.

These results are indicative for a further improved effect provided by the administration of non-digestible oligosaccharides plus BbC50cf and St065cf on Th1 response increase. The observed effect is indicative for the advantageous use of a combination of i) at least two different non-digestible carbohydrates, ii) a product obtained by incubating an aqueous substrate with bifidobacteria, subsequently inactivating by heating the incubated mixture and/or removing the bifidobacteria cells by centrifugation and/or centrifugation and iii) a product obtained by incubating an aqueous substrate with streptococci, subsequently inactivating by heating the incubated mixture and/or removing the streptococci cells by centrifugation and/or centrifugation, in the present uses.

TABLE 2

DTH response

| Group: | Mean DTH μm (S.E.) | Δ DTH μm | Relative DTH |
|---|---|---|---|
| Sham | 24.3 (0.6) | 0 | 0 |
| Placebo | 66.5 (0.3) | 42.2 | 1.00 |
| BbC50cf + GF | 108.9 (0.3)* | 84.6 | 2.00 |
| BbC50cf + St065cf | 113.6 (0.3)* | 89.3 | 2.12 |
| BbC50cf + GF + St065cf | 147.6 (0.2)* $^a$ | 123.2 | 2.92 |

*$p < 0.05$ compared with placebo
$^a$ $p < 0.05$ compared with Bbc50f + GF and with Bbc50f + St065cf Example 5: Synergistic Effect of the Incubated Product and Non-Digestible Carbohydrates on Decrease of Th2 Response Methods The effect of diets comprising (a) BbC50cf prepared according to example 1; (b) a combination of non-digestible carbohydrates (GF) containing galacto-oligosaccharides (Elixor) and fructo-oligosaccharides (Raftilin HP); and (c) a combination of (a) and (b), i.e. comprising step c) of the present process, were tested in a mouse model wherein a response to an allergen is measured by an immediate type hypersensitivity (ITH) response. This ITH response in the ears after challenge with an allergen in the lungs is a measure of an increased Th2 response. During response to the allergen in the lungs, masts cell almost immediately degranulate systemically, including in the ears. These reactions all involve IgE, which in its turn requires a Th2 response during helper T cell development. Therefore an enhanced ITH is indicative of increased IgE and hence increased Th2 response.

Specific pathogen free male BALB/c mice were obtained from Charles River (Maastricht, the Netherlands). Food and water was provided ad libitum and the mice were used when 6-9 weeks of age. Ovalbumin (grade V) and acetyl-β-methylcholine chloride (methacholine) were purchased from Sigma Chemical Co. (St. Louis, Mo., USA). Aluminium hydroxide (AlumImject) was purchased from Pierce (Rockford, Ill., USA).

The same diets as in example 2 were tested for 14 days prior to OVA sensitisation until the end of the experiment. Mice were sensitised by two i.p. injections with 10 μg ovalbumin adsorbed onto 2.25 mg aluminium hydroxide in 100 μl saline or saline alone on days 0 and 7. Mice were challenged on days 35, 38, and 41 by inhalation of ovalbumin aerosols in a plexiglass exposure chamber for 20 minutes. The aerosols were generated by nebulising an ovalbumin solution (10 mg/ml) in saline using a Pari LC Star nebulizer (Pari respiratory Equipment, Richmond, Va., USA). ITH was measured after 1 h after challenge with the allergen ovalbumin.

Results

The results on ITH are shown in table 3:

TABLE 3

ITH response

| Group: | Mean ITH μm (S.E.) | Δ ITH μm | Relative ITH |
|---|---|---|---|
| control | 104.3 (3.8) | 0 | 0 |
| Placebo | 184.7 (8.7) | 80.4 | 1 |
| GF | 159.8 (17.9)* | 55.5 | 0.69 |
| BbC50cf | 173.1 (20.3) | 68.8 | 0.86 |
| GF + BbC50cf | 136.6 (14.4)** | 32.3 | 0.40 |
| GF + BbC50cf theoretically | 151.7 | 47.4 | 0.59 |

*significantly different from control (*$P < 0.05$ and **$P < 0.01$).

The diets containing dosages of 1 wt. % GF or 3 wt. % BbC50cf both induced a small decrease in the ITH response. The combination of 1 wt. % GF plus 3 wt. % BbC50cf induced a statistically significant decrease of about 60% in the ITH response (see Table 3). As the effect is significantly higher than the ITH responses from diets containing the oligosaccharides alone, and also much higher than based on the additive effect of GF and BbC50cf, which can be calculated to be about 40% decrease of ITH, these results are indicative for the synergistic effect provided by the administration of non-digestible oligosaccharides and incubated product on lowering of the Th2 response.

The observed effect is indicative for the advantageous use of a combination of non-digestible carbohydrates and a product obtained by incubating a substrate with bifidobacteria and subsequently inactivating and/or removing the bifidobacteria in the present uses. The results of this experiment are an indication that the present invention can advantageously be used for support in prevention and/or treatment of in particular asthma, allergy, atopic dermatitis, allergic conjunctivitis, dust mite allergy, urticaria and allergic rhinitis.

Example 6: Infant Milk Formula

An infant milk formula was prepared by mixing the following ingredients: demineralised whey, vegetable fat, lactose, skim milk, non-digestible carbohydrates, whey protein concentrate, fish oil, minerals, vitamins.

The skim milk was pre-incubated in the manner described in example 1.

The concentration of the preparation obtained by incubation with *Bifidobacterium breve* in step a) and b) was 15.6 wt. % based on dry weight of the infant formula.

No living bifidobacteria were detected in the final product.

The final composition of the infant formula comprised per 100 ml:
- 66 kcal
- 1.3 g milk protein (casein and whey protein).
- 7.3 g digestible carbohydrates (mainly lactose)
- 3.5 g fats (mainly vegetable fats)
- 0.8 g trans-galactoligosaccharides (source VivinalGOS) and polyfructose (source raftilinHP)
- Trace elements, minerals, vitamins and other micronutrients as known in the art.

The infant milk formula claims to strengthen the immune system and/or to lower the incidence of atopic eczema and/or to reduce the incidence of infections and/or reduce the incidence on allergy.

Example 7: Infant Milk Formula

Pasteurized skimmed cow's milk was concentrated by evaporation to about 43 wt. % dry matter based on weight of the skimmed cow's milk. The concentrate was cooled to about 37° C., was then inoculated with about 10% (v/w) *B. breve* CNCM I-2219 culture comprising $3 \times 10^9$ cfu per ml. This inoculum was prepared as known in the art. The initial pH was between 6-7.1. After incubating for 8 h at 37° C., in a tank with periodic stirring for 10 minutes every 2 hours, the pH stayed between 6-7.1 and the *B. breve* population was about $10^6$ bacteria/ml (step (a)).

A pre-warmed inoculum was prepared from *S. thermophilus* CNCM I-1620 culture by maintaining a frozen inoculum for about 7 h at about 40° C. Pasteurized lactose solution (between 350 and 450 g/l) was cooled to about 45 and 55° C., and then inoculated with about 10 (v/w) *S. thermophilus* CNCM I-1620 pre-warmed inoculum comprising about $3 \times 10^9$ cfu per ml. The initial pH was about pH 6. After incubating for about 7 h at about 50° C., in a tank with periodic stirring for 10 minutes every 2 hours, the pH was kept constant between 6-8 and the *S. thermophilus* population was about $10^6$ bacteria/ml (step (d)).

Both incubated preparations, skim milk, vegetable fat, malto-dextrin, trans-galacto-oligosaccharides and fructo-oligosaccharides oligosaccharides, and other ingredients well known for infant milk formula (such as vitamins, minerals, trace elements) were mixed (step c, f). The mixture was pasteurized (step b, e) and subsequently spray-dried.

Final composition of the infant formula comprising per 100 ml:
- 68 kcal
- 1.45 g protein (casein and whey protein from milk; partially hydrolysed)
- 8.6 g digestible carbohydrates (mainly lactose and malto-dextrin)
- 3.1 g fats (mainly vegetable fats)
- 0.8 g trans-galactoligosaccharides (source VivinalGOS) and polyfructose (source raftilinHP)
- Trace elements, minerals, vitamins and other micronutrients (taurine, choline, inositol, nucleotides, carnitine) as known in the art.

The invention claimed is:

1. A nutritional composition obtained by a process comprising:
   (a) inoculating bifidobacteria in an aqueous substrate in amount of between $1 \times 10^7$ to $1 \times 10^{11}$ cfu bifidobacteria/ml, the aqueous substrate having a pH of between 4 and 8, and comprising at least one of milk, milk protein, whey, whey protein, whey protein hydrolysate, casein hydrolysate, and lactose;
   (b) incubating the bifidobacteria in the aqueous medium, under aerobic or anaerobic conditions and at a temperature of 20° C. to 50° C., for at least 2 h, to obtain a first incubated mixture;
   (c) inactivating bifidobacteria from the first incubated mixture; and
   (d) combining the incubated mixture with fructo-oligosaccharides and galacto-oligosaccharides,
   wherein the nutritional composition comprises less than $10^3$ cfu living Bifidobacteria per g dry weight of the preparation.

2. The nutritional composition according to claim 1, having a viscosity of 1 to 60 mPa·s at a shear rate of 100 s−1 at 20° C.

3. The nutritional composition according to claim 1, wherein the bifidobacteria are inactivated by heat treatment.

4. A nutritional composition comprising, based on total dry weight of the composition:
   (a) 0.5 to 10 wt. % of the sum of galacto-oligosaccharides and fructo-oligosaccharides, and
   (b) 5 to 99.5 wt. % of a preparation obtained by a process comprising:
      (i) inoculating bifidobacteria in an aqueous substrate in amount of between $1 \times 10^7$ to $1 \times 10^{11}$ cfu bifidobacteria/ml, said aqueous substrate having a pH of between 4 and 8, and comprising at least one selected from the group consisting of milk, milk protein, whey, whey protein, whey protein hydrolysate, casein hydrolysate, and lactose;
      (ii) incubating the bifidobacteria in the aqueous medium, under aerobic or anaerobic conditions and at a temperature of 20° C. to 50° C., for at least 2 h, to obtain a first incubated mixture;
      (iii) inactivating the bifidobacteria from the first incubated mixture; and
      (iv) combining the incubated mixture with fructo-oligosaccharides and galacto-oligosaccharides,
   wherein the bifidobacteria in (i) belong to the species *B. breve*, and
   wherein the nutritional composition comprises less than $10^3$ cfu living Bifidobacteria per g dry weight of the preparation.

5. The nutritional composition according to claim 4, wherein the bifidobacteria are inactivated by heat treatment.

6. The nutritional composition according to claim 4, further comprising (c) 2 to 94.5 wt. % of the preparation obtained by:
   (v) incubating *Streptococcus thermophilus*, with a substrate selected from the group consisting of milk, milk protein, whey, whey protein, whey protein hydrolysate, casein, casein hydrolysate, and lactose, to obtain a second incubated mixture;
   (vi) optionally inactivating the *S. thermophilus* by heating the second incubated mixture of (v); and
   (vii) combining the first and second incubated mixtures.

7. The nutritional composition according to claim 6, wherein the *S. thermophilus* is inactivated by heating the second incubated mixture of (v).

8. The composition according to claim 4, wherein any non-digestible oligosaccharides are only added during combining step (iv).

9. The composition according to claim 1, wherein any non-digestible oligosaccharides are only added during combining step (d).

* * * * *